United States Patent
Turos et al.

(10) Patent No.: US 9,533,051 B2
(45) Date of Patent: Jan. 3, 2017

(54) MENTHOL-BASED NANOPARTICLES FOR DRUG DELIVERY

(71) Applicants: Edward Turos, Wesley Chapel, FL (US); Faeez Sisan Mahzamani, Brandon, FL (US); Ashleigh Brooke Bachman, Lutz, FL (US); Kristy Lineth Flores, Tampa, FL (US)

(72) Inventors: Edward Turos, Wesley Chapel, FL (US); Faeez Sisan Mahzamani, Brandon, FL (US); Ashleigh Brooke Bachman, Lutz, FL (US); Kristy Lineth Flores, Tampa, FL (US)

(73) Assignee: University of South Florida, Tampa, FL (US)

(*) Notice: Subject to any disclaimer, the term of this patent is extended or adjusted under 35 U.S.C. 154(b) by 0 days.

(21) Appl. No.: 14/958,401

(22) Filed: Dec. 3, 2015

(65) Prior Publication Data

US 2016/0158364 A1   Jun. 9, 2016

Related U.S. Application Data

(60) Provisional application No. 62/086,778, filed on Dec. 3, 2014.

(51) Int. Cl.
| | | |
|---|---|---|
| *A61K 9/50* | (2006.01) | |
| *A61K 47/32* | (2006.01) | |
| *A61K 31/43* | (2006.01) | |
| *A61K 9/107* | (2006.01) | |

(52) U.S. Cl.
CPC ............ *A61K 47/32* (2013.01); *A61K 9/1075* (2013.01); *A61K 31/43* (2013.01)

(58) Field of Classification Search
None
See application file for complete search history.

(56) References Cited

U.S. PATENT DOCUMENTS

| | | | | |
|---|---|---|---|---|
| 6,383,500 B1* | 5/2002 | Wooley | ............... | C08J 3/246 |
| | | | | 424/401 |
| 2003/0152623 A1* | 8/2003 | Bromberg | ............. | A61K 8/042 |
| | | | | 424/468 |

OTHER PUBLICATIONS

Gries, Preparation of Gold Nanoparticle—Poly( L-menthyl methacrylate) Conjugates via ATRP Polymerization, 2011.*

* cited by examiner

*Primary Examiner* — Robert A Wax
*Assistant Examiner* — Quanglong Truong
(74) *Attorney, Agent, or Firm* — Saliwanchik, Lloyd & Eisenschenk

(57) ABSTRACT

The subject invention pertains to formulations comprising poly(menthyl acrylate) nanoparticles comprising at least one active ingredient contained in a plurality of hydrophobic carriers and dispersed in an aqueous medium. The subject invention further pertains to methods of polymerization of drug loaded nanoparticles made up of methyl acrylate monomers in an aqueous emulsion.

12 Claims, 16 Drawing Sheets

| Particle | Zeta potential | Conductance x10² |
|---|---|---|
| NanopA | -64.3mV | 5.04 uS/cm |
| NanopB | -63.4mV | 5.96 uS/cm |
| NanopC | -64.1mV | 6.14 uS/cm |
| NanopD | -65.5mV | 6.04 uS/cm |
| NanopE | -52.4mV | 7.36 uS/cm |
| NanopF | -59.2mV | 6.96 uS/cm |

MENTHOL-BASED NANOPARTICLES FOR DRUG DELIVERY

CROSS-REFERENCE TO RELATED APPLICATION

This application claims the benefit of U.S. Provisional Application Ser. No. 62/086,778, filed Dec. 3, 2014, which is hereby incorporated by reference in its entirety.

BACKGROUND OF THE INVENTION

There has been increasing interest within the scientific community in the use of nanoparticles. With easily altered frameworks, these nanoparticles can be manipulated for various properties and diverse applications. One area of focus is the study of nanoparticles as a system for drug delivery. The growing antibiotic resistance of harmful microbes, such as methicillin-resistant *Staphylococcus aureus* (MRSA), has emerged as one of the dominating concerns of today's public health system, causing scientists to look for ways to circumvent this resistance through drug delivery methods and systems.

BRIEF SUMMARY OF THE INVENTION

Aspects of the present invention provide formulations comprising poly(menthyl acrylate) nanoparticles comprising at least one active ingredient contained in a plurality of hydrophobic carriers and dispersed in an aqueous medium. In some embodiments, the at least one active ingredient is an antibiotic, such as but not limited to, penicillin. The active ingredient can be from about 1% to about 20% (w/w) of the formulation. In some embodiments, the hydrophobic carriers are made up of a surfactant, such as but not limited to, sodium dodecyl sulfate (SDS). The hydrophobic carriers may form micelles dispersed in the aqueous medium such that the micelles encapsulate the poly(menthyl acrylate) nanoparticles and active ingredient(s).

In one embodiment, the poly(menthyl acrylate) nanoparticles are poly(L-menthyl acrylate) nanoparticles. In another embodiment, the poly(menthyl acrylate) nanoparticles are poly(D-menthyl acrylate) nanoparticles.

Additional aspects of the present invention provide methods of polymerization of drug loaded nanoparticles in an aqueous emulsion, comprising: adding a plurality of methyl acrylate monomers to an aqueous medium; adding an active ingredient to the aqueous medium; adding a surfactant to form the aqueous emulsion; and adding a radical initiator for alkene polymerization of the methyl acrylate monomers in the presence of the active ingredient.

In some embodiments, the menthyl acrylate monomers are selected from L-menthyl acrylate monomers, D-menthyl acrylate monomers, and a combination thereof.

DETAILED DISCLOSURE OF THE INVENTION

Figure 1:
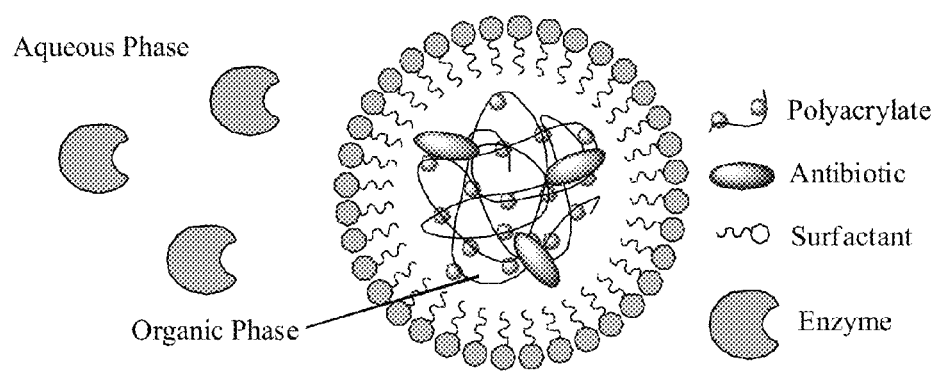
FIG. 1 shows a diagram of the organization of nanoparticles of the invention within an aqueous bulk media of the emulsion. Note: the antibiotic is not covalently bound to the polymer backbone, allowing for easier release of the drug.

The present invention provides the chemical synthesis and characterization of organic nanoparticles using menthyl acrylate as a monomer in emulsion polymerization. Either the D- or the L-stereomeric form of menthyl acrylate can be used as a means to produce homochiral polyacrylate nanoparticles in an aqueous emulsion. The present invention further provides the use of these nanoparticles to uptake chiral drug molecules (active ingredients), such as penicillin G, non-covalently, through encapsulation, at much higher concentrations compared to non-menthyl acrylate based nanoparticle formulations, as illustrated in FIG. 1. Additionally, the nanoparticles can be made and/or utilized without containing an "active ingredient".

Reference is made herein to particular features (including method steps) of the invention. Where a particular feature is disclosed in the context of a particular aspect or embodiment of the invention, that feature can also be used, to the extent possible, in combination with and/or in the context of other particular aspects and embodiments of the invention, and in the invention generally.

The term "comprises" is used herein to mean that other ingredients, components, steps, etc. are optionally present. When reference is made herein to a method comprising two or more defined steps, the steps can be carried out in any order or simultaneously (except where the context excludes that possibility), and the method can include one or more steps which are carried out before any of the defined steps, between two of the defined steps, or after all of the defined steps (except where the context excludes that possibility).

This invention may be embodied in many different forms and should not be construed as limited to the embodiments set forth herein. Rather, these embodiments are provided so that this disclosure will convey preferred embodiments of the invention to those skilled in the art.

Aspects of the present invention provide formulations comprising poly(menthyl acrylate) nanoparticles comprising at least one active ingredient contained in a plurality of hydrophobic carriers and dispersed in an aqueous medium.

As used herein, the term "pharmaceutically active ingredient" or "active ingredient" means an ingredient in the formulation that produces a physiological effect in the user. Active ingredients include, but are not limited to, antibiotics, analgesics, anti-inflammatories, stimulants, depressants, sedatives, electrolytes, vitamins, minerals, hormones, peptides, nucleic acids, or any other pharmaceutically active substances and drugs. In some embodiments, the at least one active ingredient is an antibiotic, such as but not limited to, penicillin. The active ingredient can be from about 1% to about 20% (w/w) of the formulation; however, the concentration range may be expanded or contracted, depending on the particular active ingredient.

In some embodiments, the hydrophobic carriers are made up of a surfactant, such as but not limited to, sodium dodecyl sulfate (SDS). The hydrophobic carriers may form micelles dispersed in the aqueous medium such that the micelles encapsulate the poly(menthyl acrylate) nanoparticles and active ingredient(s). Generally, the hydrophobic carriers comprise amphiphilic properties. A micelle is formed from amphiphilic molecules. When dispersed in an aqueous solution, the hydrophilic head groups form a hydrophobic pocket composed of the hydrophobic tail groups. One or more active ingredients and nanoparticles may be encapsulated by the micelle in the hydrophobic pocket.

In one embodiment, the poly(menthyl acrylate) nanoparticles are poly(L-menthyl acrylate) nanoparticles. In another embodiment, the poly(menthyl acrylate) nanoparticles are poly(D-menthyl acrylate) nanoparticles.

Additional aspects of the present invention provide methods of polymerization of drug loaded nanoparticles in an aqueous emulsion, comprising: adding a plurality of methyl acrylate monomers to an aqueous medium; adding an active ingredient to the aqueous medium; adding a radical initiator for alkene polymerization of the methyl acrylate monomers in the presence of the active ingredient; and adding a surfactant to form the aqueous emulsion.

Generally, a plurality of methyl acrylate monomers is dispersed in an aqueous medium. Then, the active ingredient is dispersed into the medium containing the monomers. Next, a surfactant is added to the aqueous medium to form an emulsion containing micelles encapsulating the nanopolymer-active ingredient mix. Finally, alkene polymerization is initiated to generate the nanopolymers in the presence of the active ingredient.

In some embodiments, the methyl acrylate monomers are selected from L-menthyl acrylate monomers, D-menthyl acrylate monomers, and a combination thereof. In additional embodiments, the emulsions of the present invention can also contain variable ratios of styrene as a co-monomer for polymerization.

In some embodiments, the emulsions of the present invention comprise butyl acrylate with styrene (no menthyl acrylate). In some embodiments, the emulsions of the present invention comprise L-menthyl acrylate with styrene. In some embodiments, the emulsions of the present invention comprise D-menthyl acrylate with styrene. In some embodiments, the emulsions of the present invention comprise racemic menthyl acrylate with styrene. Additionally, the emulsions may comprise about 10, 20, 30, 40, 50, 60, 70, 80, 90, or about 100 w/w % of menthyl acrylate relative to styrene.

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

Example 1

Analysis Studies of Enantiomerically Pure Polyacrylate Nanoparticles

Figure 2:
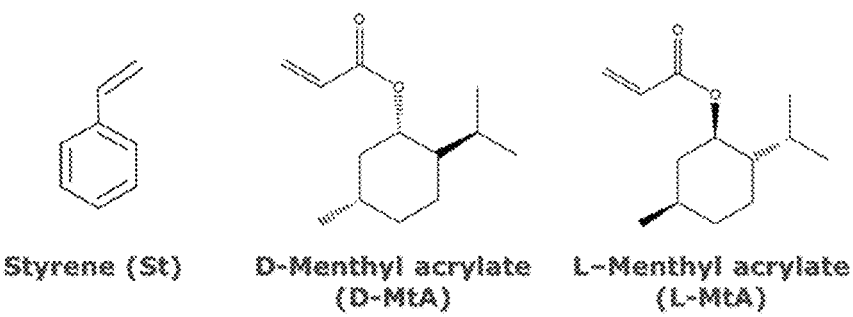
FIG. 2 illustrates acrylate monomers of the present invention.

Purely organic chiral nanoparticles were synthesized from polyacrylates. Polyacrylates contain a large diverse group of potential monomers, each with readily tunable physical properties. Chirality was imparted via polymerization of styrene (St) with chiral monomer, L-menthyl acrylate (L-Mta) (FIG. 2). The L-Mta was synthesized as follows:

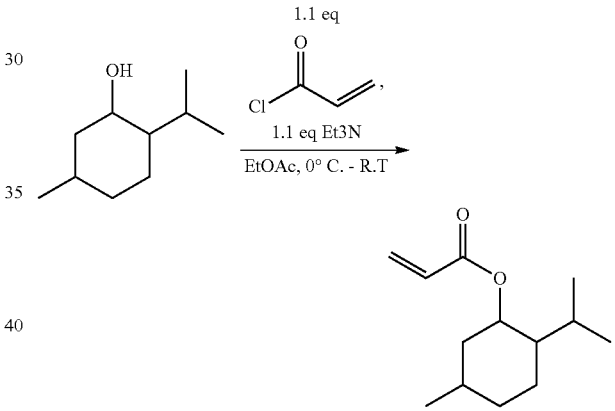

Figure 3:
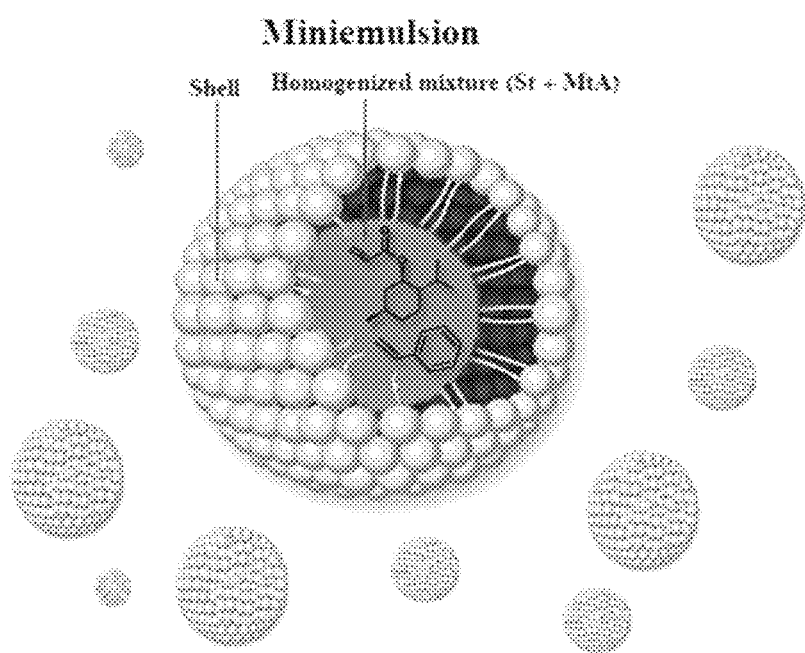
FIG. 3 illustrates miniemulsion polymerization structures.

The mechanism behind the nanoparticle formation is miniemulsion polymerization. Surfactants behave as reaction vesicles to contain the polymerization (FIG. 3). The chirality may be tailored by varying the chiral monomer and its concentration.

Figure 4:
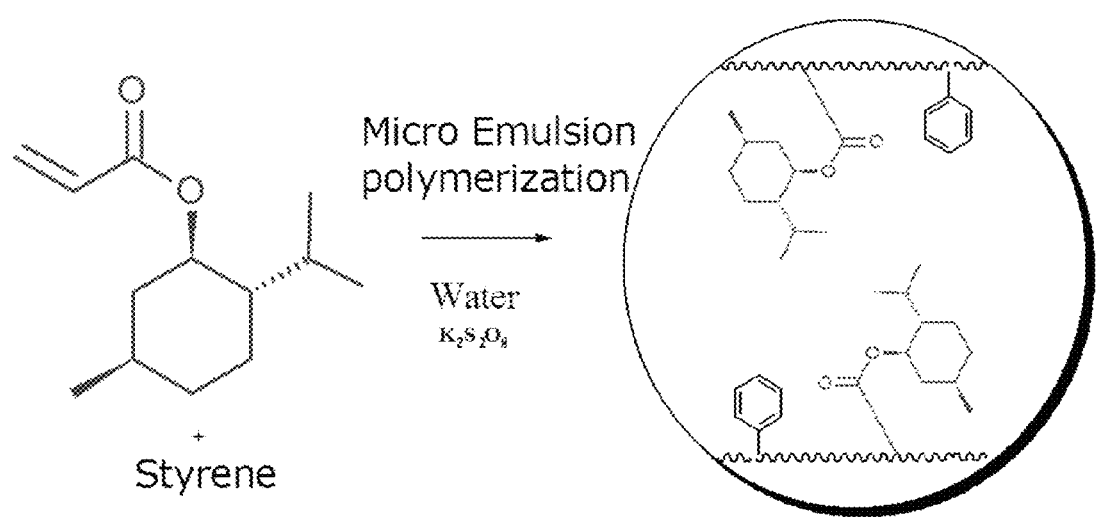
FIG. 4 illustrates a miniemulsion polymerization process.

Six samples of poly (MtA-co-St) nanoparticles were synthesized using 10, 20, 30, 40, 50, and 60 v/v % of MtA relative to St (FIG. 4).

As shown in Tables 1 and 2, poly(MtA-co-St) form as stable nanoparticle emulsions in water.

TABLE 1

Nanoparticle emulsions

| Particle | MtA:St | MtA % |
|---|---|---|
| NanopA | 1:9 | 10% |
| NanopB | 2:8 | 20% |
| NanopC | 3:7 | 30% |
| NanopD | 4:6 | 40% |
| NanopE | 5:5 | 50% |
| NanopF | 6:4 | 60% |

TABLE 2

Zeta potential provide stability guidelines for colloids

| Zeta Potential (±mV) | Stability of Colloid |
|---|---|
| 0-5 | Rapid coagulation |
| 10-30 | Partial stability |
| 30-40 | Moderate stability |
| 40-60 | Good stability |
| >60 | Excellent stability |

Figure 5:
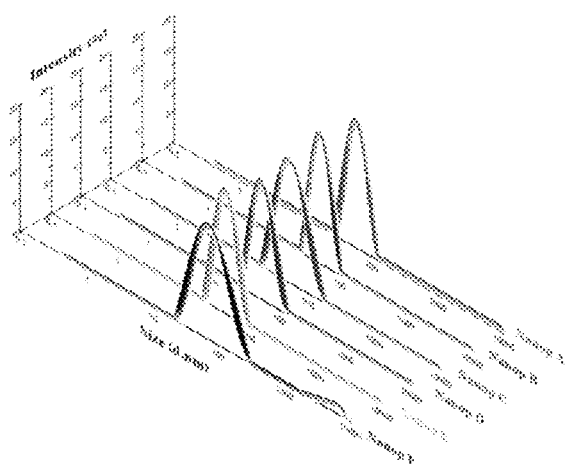
FIG. 5 shows distribution of particle sizes and stability of nanoparticles of the present invention.

Optical activity was determined by polarimetry and particle size, stability, and polydispersity determined by dynamic light scattering. The distribution of particle size and particle stability is shown in FIG. 5.

Figure 6:
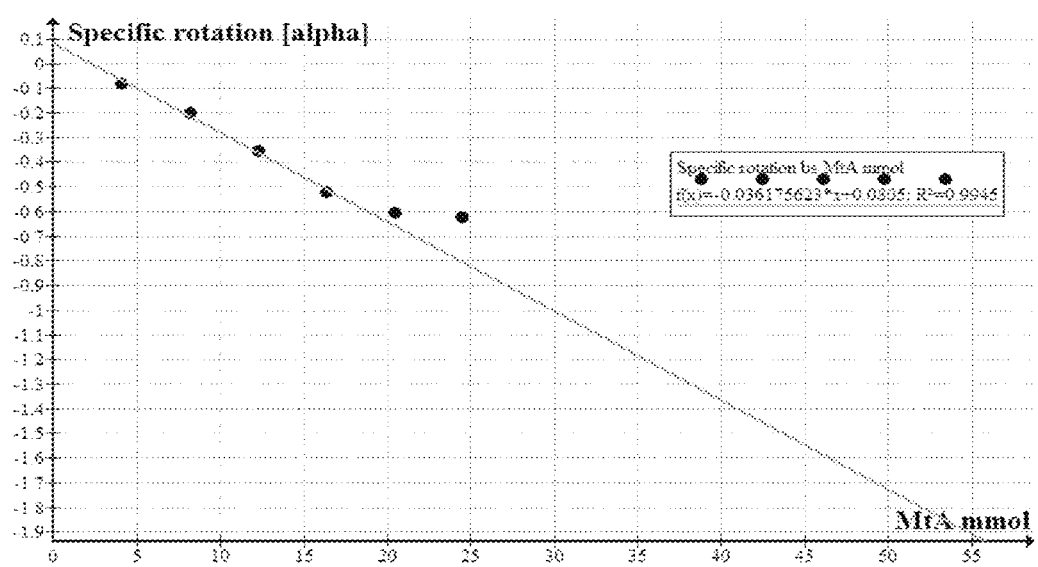
FIG. 6 is a graph showing that the nanoparticle emulsions have optical activity and that the specific rotation values are somewhat non-linear.

The bioactivity was tested by Kirby-Bauer diffusion assay against *Staphylococcus aureus*. FIG. 6 shows that the nanoparticle emulsions have optical activity and, thus, are chiral and that the specific rotation values are somewhat nonlinear.

Example 2

Analysis of Emulsion Stability and Uniformity of Chiral Polymer Nanoparticles In this example, the particle size and zeta potential are characterized for optically active polyacrylate nanoparticles derived from D- and L-menthyl acrylate.

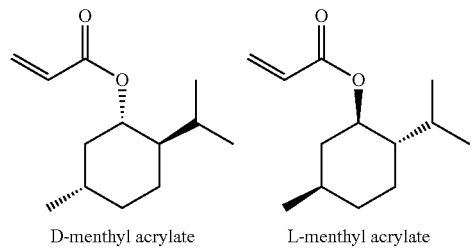

D-menthyl acrylate    L-menthyl acrylate

The enantiomerically-pure acrylates of D- and L-menthol were synthesized by reaction with acryloyl chloride in the presence of triethylamine.

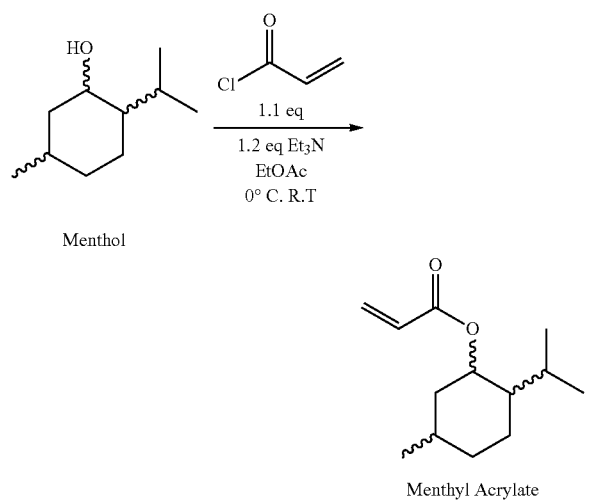

Menthol

Menthyl Acrylate

Figure 7:
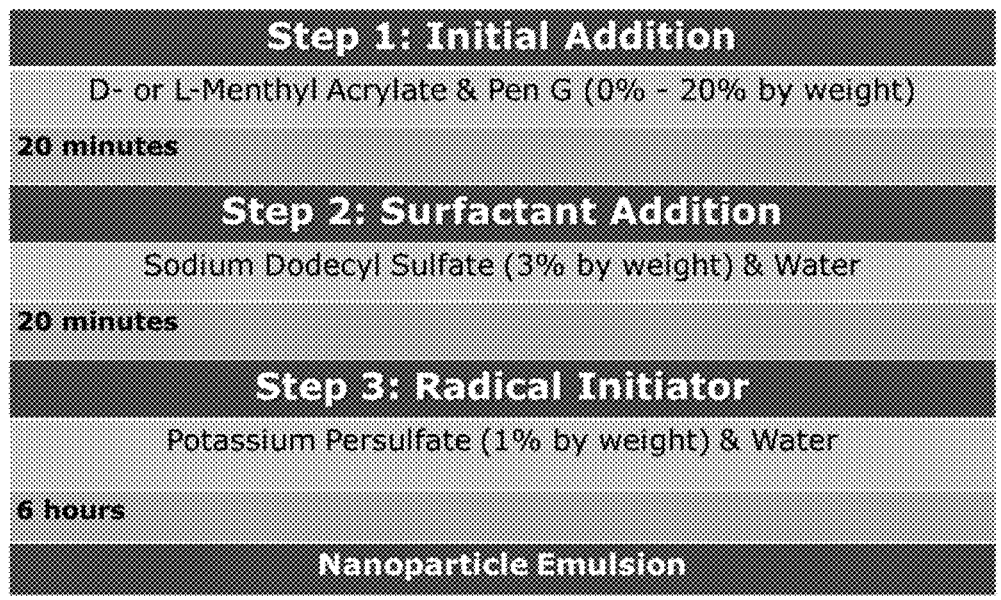
FIG. 7 shows the process of polymerization of nanoparticles from polyacrylate monomers.
Figure 7:
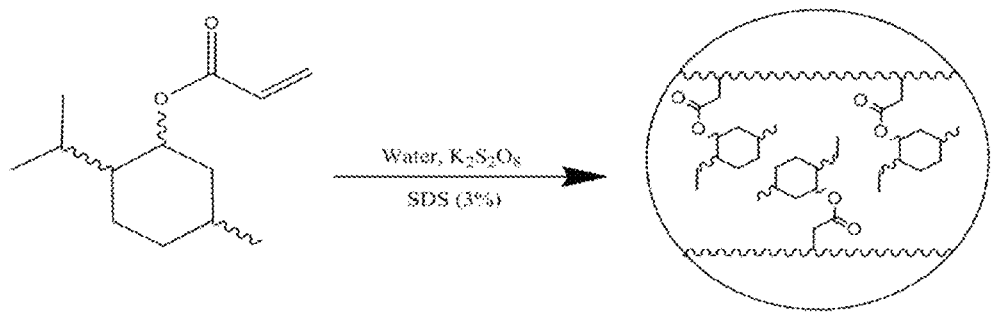

The chiral nanoparticles were then synthesized by emulsion polymerization of the D- and L-menthyl acrylates, using styrene as a co-monomer at 78 degrees Celsius. Potassium persulfate was used as a radical initiator and sodium dodecyl sulfate (SDS) was added as a surfactant to stabilize the nanoparticles (FIG. 7). A summary of the reagents and the necessary amounts for the synthesis of a 2.5 mL emulsion sample at 3% drug load concentration is shown in Table 3.

TABLE 3

| Compound | Amount |
|---|---|
| Menthyl acrylate | 0.5 mL |
| Pen G (3% solution) | 15 mg |
| SDS (3%) | 15 mg |
| Potassium persulfate (1%) | 5 mg |
| Water | 2.0 mL |
| Total Volume | 2.5 mL |

Six series of nanoparticle samples were prepared for physical characterization:

(1) butyl acrylate with styrene (no menthyl acrylate)
(2) L-menthyl acrylate with styrene
(3) D-menthyl acrylate with styrene
(4) racemic menthyl acrylate with styrene Each of these four series contained ten samples with 10, 20, 30, 40, 50, 60, 70, 80, 90, and 100 w/w % of menthyl acrylate relative to styrene.

(5) nanoparticles made by polymerizing mixtures of the enantiomeric pure acrylates, in ratios from 90:10 D:L to 10:90 D:L (BE "before emulsification") (no styrene)
(6) nanoparticles made by mixing different amounts of each enantiomeric pure nanoparticle emulsion, in ratios from 90:10 D:L to 10:90 D:L (AE "after emulsification")" (no styrene)

Each of these two series contained 9 samples with 10, 20, 30, 40, 50, 60, 70, 80, and 90 w/w % of D-menthyl acrylate relative to L-menthyl acrylate.

Figure 8:
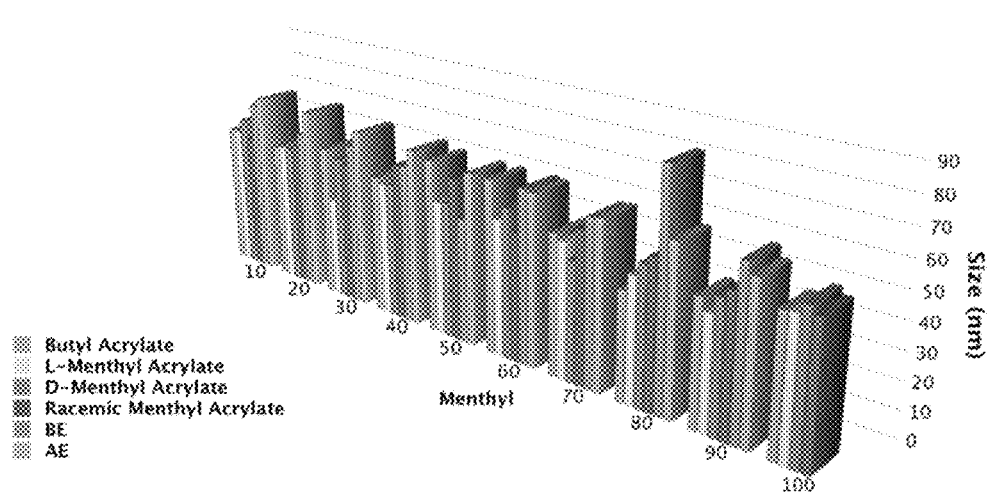
FIG. 8 shows a graph of the distribution of particle sizes of various chiral nanoparticle samples of the present invention.
Figure 9:
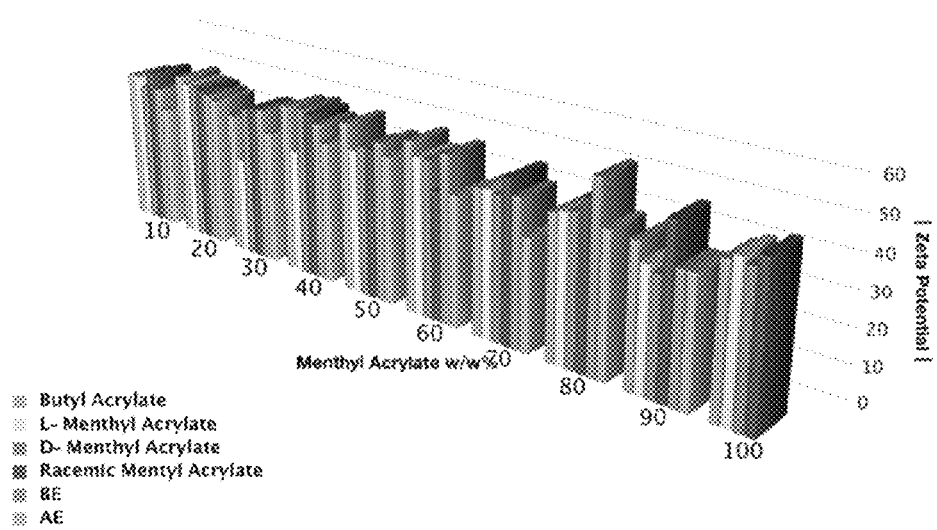
FIG. 9 shows a graph of the distribution of zeta potentials of various chiral nanoparticle samples of the present invention.

For each of the nanoparticle samples, dynamic light scattering was used to analyze the particle size, uniformity, and stability, in triplicates. The data for each of these are presented in FIGS. 8 and 9. The particle size is measured in nanometers (nm), which includes the nanoparticle as well as the surface hydration sphere. The narrowness of size distribution ensures that the nanoparticles are uniform in size. A large zeta potential value greater than 60 mV indicates the emulsion is very stable and does not precipitate (see Table 2).

This example demonstrates that chiral polyacylate nanoparticles can be synthesized by using enantiomerically pure menthyl acrylates as monomers. There were no significant differences observed in the particle sizes or stabilities as the amounts of chiral monomers were varied. The particle sizes ranged from 40-60 nm among all series, and the zeta potentials were in the range of −30 to −50 mV, indicating high stability in aqueous emulsions.

Example 3

Study of the Optical Properties of Chiral Polyacrylate Nanoparticles Synthesized from D- and L-Menthyl Acrylate In this example, chirality is added to the framework using enantiomerically-pure acrylates of D- and L-menthol as shown below, and the optical properties of the chiral nanoparticles are characterized by polarimetry and circular dichroism.

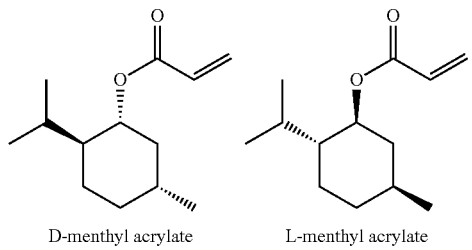

D-menthyl acrylate          L-menthyl acrylate

The enantiomerically-pure acrylates of D- and L-menthol were synthesized by reaction with acryloyl chloride in the presence of triethylamine.

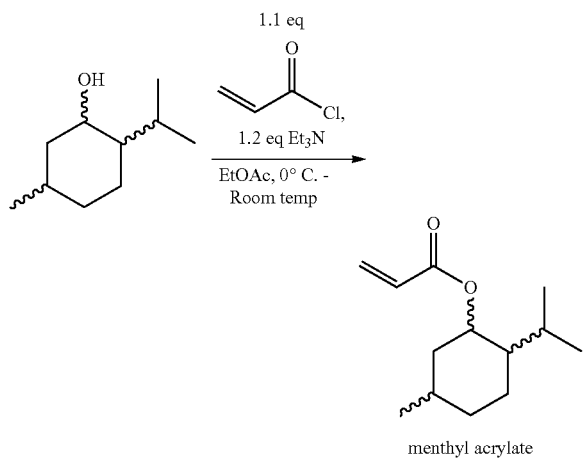

menthyl acrylate

With the L-menthyl acrylate and D-menthyl acrylate being used as monomers, different nanoparticles were prepared using varying amounts of each chiral acrylate, from 0% to 100% by weight. The acrylate and styrene were used as co-monomers to construct the nanoparticles by free radical polymerization in aqueous solution.

Ten samples of each nanoparticle emulsion were synthesized with the varying ratios by w/w % of the chiral acrylate monomer and the styrene. Each sample was then diluted 200 times for measurements in both the polarimeter and CD.

Optical activity was determined by optical polarimetry and circular dichroism (CD). All optical rotation measurements on the polarimeter were recorded at 589 nm. A range of 195-250 nm at 1 nm intervals was used for the CD (data not shown).

Figure 10:
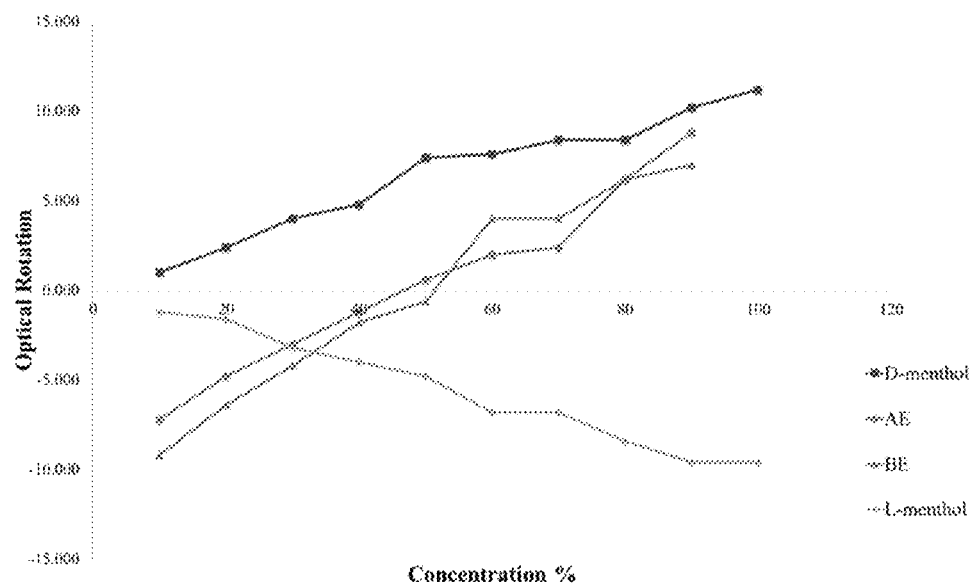
FIG. 10 shows a graph of the optical rotation versus concentration for the polyacrylated nanoparticle emulsions of the present invention.

A perfectly linear relationship was expected between the angle of rotation and concentration. However, as shown in FIG. 10, there was a slight deviation from linearity between the 60-70 w/w % for the D and L enantiomeric particles. Also in the graph, the line labeled BE (Before Emulsion) is for nanoparticle samples containing mixtures of both enantiomeric acrylates, in ratios ranging from 10D:90L to 90D:10L, prepared by emulsion polymerization of the two chiral acrylates. The line labeled AE (After Emulsion) is for nanoparticle samples consisting of mixtures of enantiomerically pure nanoparticle emulsions (each made from the individual menthyl acrylate enantiomers) ranging from 10D: 90L to 90D:10L. Neither of the BE and AE sets contained styrene but only the menthyl acrylate. These sets were synthesized to show that there is no significant difference between mixing the enantiomeric monomers then polymerizing to make the emulsions, versus mixing the pre-made chiral nanoparticle emulsions. The optical properties are similar for both samples.

This example shows that chiral polyacrylate nanoparticles can be synthesized by emulsion polymerization using enantiomerically pure menthyl acrylates as monomers. The optical activity of these chiral polyacrylated nanoparticles was analyzed using polarimetry. It was found that the optical rotation values of the nanoparticles slightly deviated from linearity for those samples having 60-70 w/w % of either D-menthyl acrylate or L-menthyl acrylate. The alternative methods used to make the BE and AE sets showed no significant differences in the optical properties of the chiral polyacrylated nanoparticles.

Example 4

Figure 11:
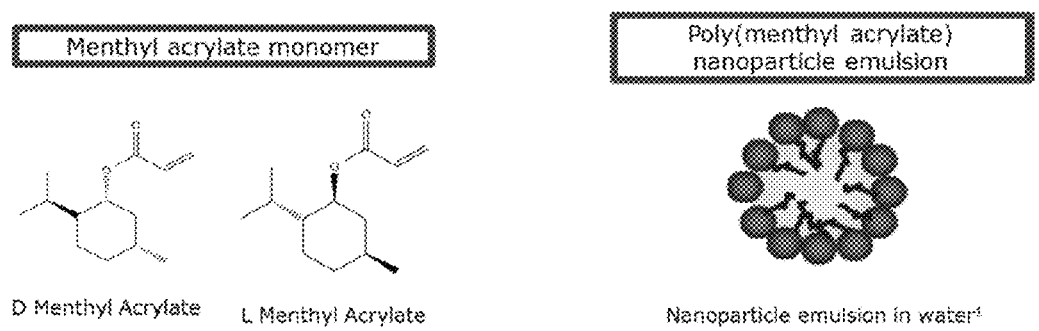
FIG. 11 illustrates menthyl acrylate monomers and acrylate nanoparticle emulsions of the present invention.

Study of the Stability and Uniformity of Enantiomerically-Pure Penicillin Encapsulated Poly(Menthyl Acrylate) Nanoparticle Emulsions In order to synthesize the menthol derived polymers, L-menthol and D-menthol were individually reacted with acryloyl chloride along with triethylamine to create the single chiral unit that makes up the polymer chain. The polymer framework was prepared using potassium persulfate as the radical initiator for the alkene polymerization. To make the emulsion, the polymer is set in the presence of the surfactant sodium dodecyl sulfate (SDS) and water (FIG. 11).

Figure 12:
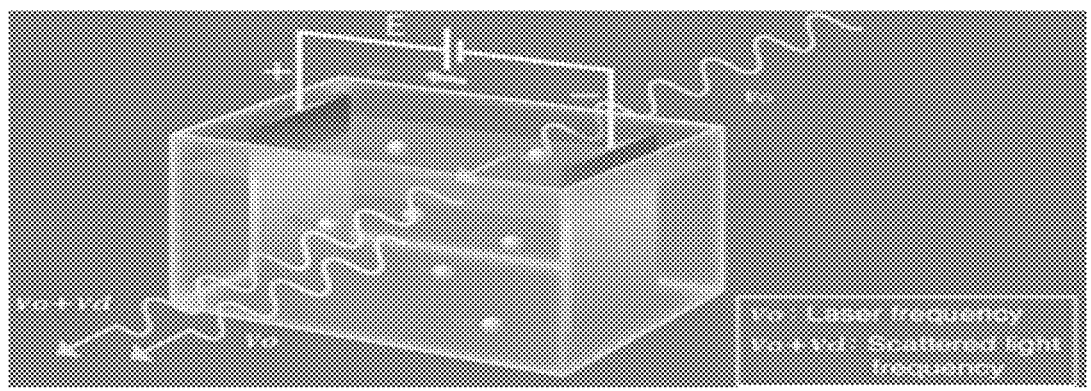
FIG. 12 illustrates a method of measuring size and stability of nanoparticles utilizing dynamic light scattering.

Nanoparticle behavior has been the subject of great scrutiny because while many methods have proven to be viable for analysis, dynamic light scattering (DLS) is one of the few that is non-destructive and employs simple methods (Livingstone, 2012). In order to analyze the nanoparticles, a beam of light is passed through the particle sample that produces a signal according to the changes in scattering intensity (FIG. 12). The scattering intensity of the sample reflects the constant movement of the nanoparticles (Livingstone, 2012).

Zeta potentials are very useful tools for the measurement of stability because they can quantify the charge repulsion or attraction between the particles involved in a liquid environment (Wang et al., 2013). Since the emulsion involves two liquids of different miscibility, the zeta potential of the encapsulated nanoparticles can be measured using a zetasizer that uses dynamic light scattering technology (Sarker, 2013). Zeta potentials can be analyzed for particle uniformity and stability based on their numerical range (Table 2). Additionally, DLS can help quantify particle size.

Each sample was prepared by encapsulating different percentages of Penicillin G within the polymer framework. The different samples were loaded starting with 1% Penicillin G (by weight) and the percentage of the antibiotic was increased by 1% in each new sample all the way up to 20% (Table 4). Each particle size including the emulsion was calculated by taking the average of 3 sample sizes in nanometers (nm). The zeta potential is the average of triplicate samples, in millivolts (mV). Furthermore, to ensure chirality was maintained the optical rotation of the nanoparticles was measured through polarimetry.

TABLE 4

| L-MENTHYL | | | D-MENTHYL | | |
|---|---|---|---|---|---|
| % of PenG | Zeta Potential (mV) | Size (nm) | Percentage of PenG | Zeta Potential (mV) | Size (nm) |
| 1% | −59.26 | 69.13 | 1% | −76.66 | 59.94 |
| 2% | −48.14 | 74.45 | 2% | −72.79 | 60.83 |
| 3% | −60.03 | 69.29 | 3% | −69.52 | 61.40 |
| 4% | −48.46 | 65.8 | 4% | −99.63 | 47.35 |
| 5% | −50.49 | 57.47 | 5% | −48.44 | 49.55 |
| 6% | −49.49 | 65.46 | 6% | −44.99 | 54.45 |
| 7% | −44.88 | 49.07 | 7% | −45.67 | 63.30 |
| 8% | −45.96 | 51.82 | 8% | −48.69 | 60.165 |
| 9% | −45.54 | 54.19 | 9% | −45.2 | 53.61 |
| 10% | −45.82 | 56.29 | 10% | −62.62 | 72.82 |
| 11% | −47.11 | 54.71 | 11% | −66.93 | 71.09 |
| 12% | −47.77 | 51.02 | 12% | −68.63 | 67.35 |
| 13% | −47.43 | 55.38 | 13% | −31.85 | 67.68 |
| 14% | −49.13 | 54.87 | 14% | −29.13 | 79.43 |
| 15% | −47.7 | 60.06 | 15% | −63.48 | 81.48 |
| 16% | −41.2 | 67.04 | 16% | −51.77 | 73.37 |
| 17% | −62.43 | 69.47 | 17% | −98.45 | 83.81 |
| 18%* | −28.53 | 81.33 | 18% | −40.47 | 86.20 |
| 19%** | −31.73 | 80.27 | 19%** | −55.33 | 0 |
| 20% | −24.37 | 87.92 | 20% | −29.05 | 95.06 |

Figure 13:
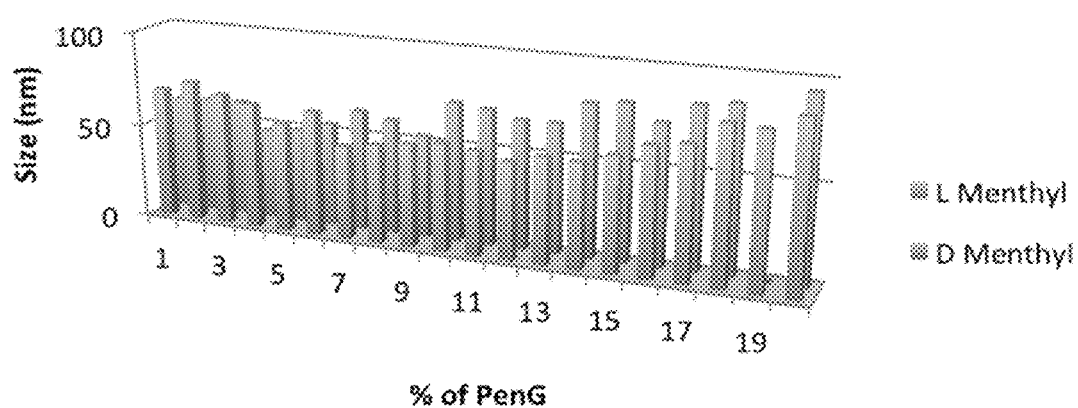
FIG. 13 shows a graph of the size distribution of penicillin encapsulated nanoparticles in nanoparticle emulsions of the present invention.

*Data average included from partial emulsion
**Data averageset includes samples with no emulsion As illustrated in FIG. 13, most of the nanoparticles were less than 100 nm. When comparing the D- and L-menthyl acrylate systems, the nanoparticle emulsions prepared using L-menthyl acrylate were more consistent in size, even when the percentage of Penicillin G was higher. Alternatively, the size of the D-menthyl-derived particles fluctuated in comparison, yet at the highest percentage of PenG, the nanoparticle was well within the range of the L-menthol sample prepared with the same percentage of PenG.

Figure 14:
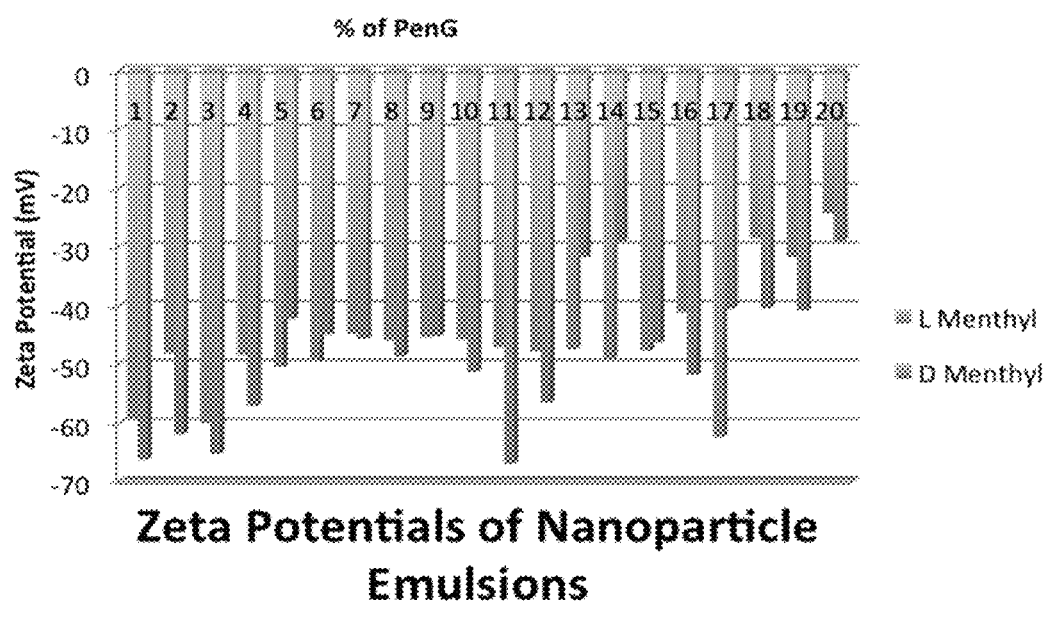
FIG. 14 shows a graph of the zeta potentials of penicillin encapsulated nanoparticles in nanoparticle emulsions of the present invention.

Zeta Potentials for both D- and L-menthyl nanoparticle emulsions (FIG. 14) showed consistent uniformity and stability with most zeta potentials being at least moderately stable. The zeta potentials for both D- and L-menthyl were as high as −24 mV but peaked at ~−63 mV on the nanoparticle made with L-menthyl. D-menthyl, however, did still show high uniformity with a particle having a value of ~−100 mV.

TABLE 5

| PenG % | L-1: Avg | L-2: Avg | D-1: Avg | D-2: Avg |
|---|---|---|---|---|
| 1 | 0 | −0.041 | 0.049 | 0.049 |
| 2 | −0.033 | −0.032 | 0.04 | 0.056 |
| 3 | −0.038 | −0.021 | 0.044 | 0.055 |
| 4 | −0.04 | −0.023 | 0.04 | 0.056 |
| 5 | −0.038 | −0.033 | 0.042 | 0.0533 |
| 6 | −0.027 | −0.038 | 0.049 | 0.0527 |
| 7 | −0.019 | −0.036 | 0.038 | 0.058 |
| 8 | −0.035 | −0.041 | 0.046 | 0.051 |
| 9 | −0.003 | −0.0423 | 0.045 | 0.049 |
| 10 | −0.04 | −0.0417 | 0.041 | 0.063 |
| 11 | −0.038 | −0.0417 | 0.015 | 0.012 |
| 12 | −0.041 | −0.036 | 0.033 | 0.008 |
| 13 | −0.038 | −0.038 | 0.0143 | 0.011 |
| 14 | −0.031 | −0.04 | 0.0137 | 0.03 |
| 15 | −0.038 | −0.037 | 0.013 | 0.019 |
| 16 | −0.029 | −0.028 | 0.007 | 0.055 |
| 17 | −0.037 | −0.006 | 0.027 | 0.058 |
| 18 | −0.034 | | 0.033 | 0.062 |
| 19 | −0.036 | | 0.014 | 0.015 |
| 20 | −0.028 | | 0.016 | 0.053 |

Figure 15:
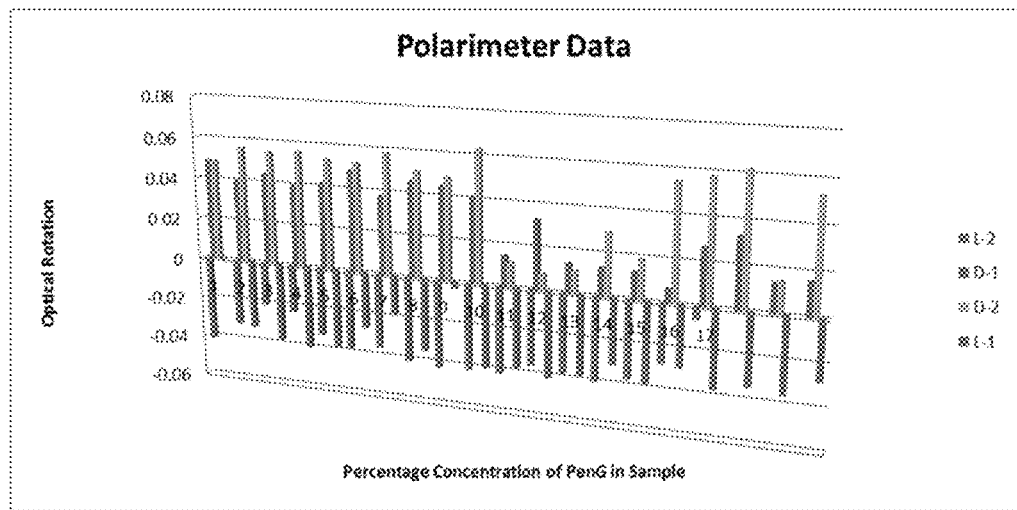
FIG. 15 shows a graph of the optical activity of penicillin encapsulated nanoparticles in nanoparticle emulsions of the present invention.

The optical rotation values of the nanoparticles were more consistent for the L-menthyl samples, which did not show a significant drop in activity at PenG concentrations of 11-15% (FIG. 15). However, the average rotation values for the D-menthyl samples were greater in magnitude than that of the L-menthyl samples (Table 5).

Since both D- and L-menthyl acrylate nanoparticles had zeta potentials ranging from ~−24 mV to ~−100 mV, the synthesized nanoparticle emulsions were consistently uniform and stable in the aqueous media. Even while the percentage of PenG increased, the uniformity of the particle remained consistent and particles such as the D-menthyl that contained 17% PenG had an excellent zeta potential close to −100 mV. While most of the tested samples appeared as single layers, one nanoparticle polymer was not emulsified D-menthyl with 19% Pen G. Additionally, some samples had partial emulsions, but the zeta potential of the nanoemulsion layer still supported uniformity. Based on the data acquired and visible uniformity of the emulsions, L-menthyl acrylate nanoparticles were more uniform. Varying zeta potentials among both menthyl enantiomers could be the subject of future study, however, based on collected data, both D- and L-menthyl acrylate nanoparticle emulsions act as viable systems for drug delivery.

Figure 16A:
FIG. 16A shows emulsions of L-menthyl acrylate with drug load concentrations of 0% to 20% of Pen G by weight (shown top) and those of D-menthyl acrylate with loads ranging from 1% to 20% of Pen G by weight (shown bottom)
Figure 16B:
FIG. 16B shows examples of failed emulsions. Note: the D-menthyl samples were more destabilized and crashed out.

The resultant nanoparticle emulsions were found to be stable both in size and zeta potential when analyzed via dynamic light scattering (DLS). There is also a definite hue to be noted as the concentration of the drug load increases in the system (FIG. 16A). Additionally, it was noted that D-menthyl acrylate emulsions were more likely to destabilize than L-menthyl acrylate emulsions (FIG. 16B).

This study demonstrated the successful synthesis of antibiotic carrying nanoparticle emulsions using a polyacrylate backbone system composed of enantiomerically pure D- and L-menthyl acrylates of up to 20% by weight. Characterization of size and stability via DLS analysis found these particles to be 100 nm in diameter, and having zeta potentials of roughly −50 mV for both enantiomers. The polarimetry measurements for optical rotation were found to be rather inconsistent across the D-Menthyl samples, with a significant drop in activity between drug load concentrations of 11-15%, and the optical activity of the L-Menthyl samples were notably smaller in magnitude than its enantiomeric counterpart. This could be due to the large dilution factor at which these samples are prepared, which introduces a large margin of error. It is also possible that the varying lengths of the polymer present in each sample had an effect on the optical activity. There were some minor destabilizing effects observed in the D-Menthyl samples in comparison to the L-Menthyl samples.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

Sarker, Dipak K. *Pharmaceutical Emulsions: A Drug Developers Toolbag*/By Dipak K. Sarker. n.p.: Chichester, West Sussex, UK: John Wiley & Sons Inc., 2013, 2013. *University of South Florida Libraries Catalog.*

Livingstone, P 2012, 'Size Matters, But So Does Stability', *R&D Magazine,* 54, 6, pp. 13-15, Business Source Premier, EBSCOhost.

Wang, N, Hsu, C, Zhu, L, Tseng, S, & Hsu, J n.d., 'Influence of metal oxide nanoparticles concentration on their zeta potential', *Journal Of Colloid And Interface Science,* 407, pp. 22-28, Science Citation Index, EBSCOhost.

We claim:

1. A formulation comprising poly(menthyl acrylate) nanoparticles comprising at least one active ingredient contained in a plurality of hydrophobic carriers dispersed in an aqueous medium.

2. The formulation of claim 1, wherein the at least one active ingredient is an antibiotic.

3. The formulation of claim 1, wherein the at least one active ingredient is penicillin.

4. The formulation of claim 1, wherein the at least one active ingredient is about 1% to about 20% (w/w) of the formulation.

5. The formulation of claim 1, wherein the plurality of hydrophobic carriers are a surfactant.

6. The formulation of claim 1, wherein the plurality of hydrophobic carriers form micelles dispersed in the aqueous medium.

7. The formulation of claim 1, wherein the poly(menthyl acrylate) nanoparticles are poly(L-menthyl acrylate) nanoparticles.

8. The formulation of claim 1, wherein the poly(menthyl acrylate) nanoparticles are poly(D-menthyl acrylate) nanoparticles.

9. A method of polymerization of drug loaded nanoparticles in an aqueous emulsion, comprising:
   adding a plurality of methyl acrylate monomers to an aqueous medium;
   adding an active ingredient to the aqueous medium;
   adding a radical initiator for alkene polymerization of the methyl acrylate monomers in the presence of the active ingredient; and
   adding a surfactant to form the aqueous emulsion.

10. The method of claim 9, wherein the menthyl acrylate monomers are L-menthyl acrylate monomers.

11. The method of claim 9, wherein the menthyl acrylate monomers are D-menthyl acrylate monomers.

12. The method of claim 9, wherein the menthyl acrylate monomers are selected from L-menthyl acrylate monomers, D-menthyl acrylate monomers, and a combination thereof.

* * * * *

UNITED STATES PATENT AND TRADEMARK OFFICE
CERTIFICATE OF CORRECTION

PATENT NO. : 9,533,051 B2  
APPLICATION NO. : 14/958401  
DATED : January 3, 2017  
INVENTOR(S) : Edward Turos et al.

Page 1 of 1

It is certified that error appears in the above-identified patent and that said Letters Patent is hereby corrected as shown below:

In the Specification

Column 9,  
Line 9, "4%" should read --4%*--.  
Line 12, "8%" should read --8%*--.  
Line 13, "9%" should read --9%*--.  
Line 16, "12%" should read --12%*--.  
Line 17, "13%" should read --13%*--.

Column 10,  
Line 66, "2013, 2013." should read --2013.--.

Signed and Sealed this  
Eighth Day of August, 2017

Joseph Matal  
*Performing the Functions and Duties of the*  
*Under Secretary of Commerce for Intellectual Property and*  
*Director of the United States Patent and Trademark Office*